United States Patent [19]
Clarke et al.

[11] Patent Number: 5,576,548
[45] Date of Patent: Nov. 19, 1996

[54] NUCLEAR IMAGING ENHANCER

[75] Inventors: Laurence P. Clarke, Temple Terrace; Wei Qian, Wesley Chapel; Maria Kallergi, Tampa, all of Fla.

[73] Assignee: University of South Florida, Tampa, Fla.

[21] Appl. No.: 464,393

[22] Filed: Jun. 5, 1995

[51] Int. Cl.$^6$ .................................................. G01T 1/20
[52] U.S. Cl. ...................... 250/369; 364/413.24; 382/261
[58] Field of Search ....................... 250/363.02, 363.04, 250/369, 370.08, 370.09; 364/413.24; 382/156, 241, 248, 261; 399/924

[56] References Cited

U.S. PATENT DOCUMENTS

| | | | |
|---|---|---|---|
| 4,654,795 | 3/1987 | Shimoni | 364/414 |
| 5,000,183 | 3/1991 | Bonnefous | 128/660.01 |
| 5,212,637 | 5/1993 | Saxena | 364/413.26 |
| 5,253,530 | 10/1993 | Letcher, III | 73/602 |
| 5,359,674 | 10/1994 | van der Wal | 382/261 |

OTHER PUBLICATIONS

Jaszcak et al., "Physical factors affecting quantitative measurements using camera-based single Photon Emission Computed Tomography (SPECT)" *IEEE Trans. Nucl. Sci.*, vol. NS-28, pp. 69–80 (Feb. 1981).

Clarke et al., "Quantitative ECT: Comparison of recovery coefficient and linearity of detector response for Single Photon and Coincidence Detection" *IEEE Transactions on Medical Imaging*, vol. 5(4), pp. 177–182 (Mar. 1986).

Clarke et al., "Bremsstrahlung imaging using the gamma camera: factors affecting attenuation" *J. Nucl. Med.*, vol. 33, pp. 161–166 (1992).

King et al., "A Wiener filter for nuclear medicine images" *Med. Phys.*, vol. 10, pp. 876–880, (1983).

Penney et al., "Modifying constrained least-squares restoration for application to Single Photon Cmission Computed Tomography Pryection Images" *Med. Phys.*, vol. 15, pp. 334–342 (1988).

Qian et al., "Order-statistic neural-network hybrid filters for gamma camera bremsstrahlung image restoration" *IEEE Trans. on Med. Imaging*, vol. 12, No. 1, pp. 58–65 (Mar., 1993).

Arce and Foster, "Detail-preserving ranked-order based filters for image processing" *IEEE Trans. Acoust., Speech, Signal Processing*, vol. 37(1), pp. 83–98, (Jan. 1989).

Zhou et al., "Image restoration using a neural network" *IEEE Trans. ASSP.*, vol. 36, pp. 1141–1151 (1988).

Li et al., "Neural network for maximum entropy restoration of nuclear medicine images" *Proceedings of the Int'l Conference on Acoustics, Speech and Signal Proc.*, Minneapolis, MN (Apr., 1993).

Abbiss et al., "Superesolution algorithms for a modified hopfield neural network" *IEEE Trans. Signal Proc.*, vol. 39, pp. 1516–1523 (1991).

(List continued on next page.)

*Primary Examiner*—David P. Porta
*Assistant Examiner*—David Vernon Bruce
*Attorney, Agent, or Firm*—Kohn & Associates

[57] ABSTRACT

A wavelet based neural network (WNN) is proposed for image restoration using a nuclear gamma camera. The WNN first segments the image noise from the detected signal using a wavelet or multi-resolution method and then restores the detector resolution using the neural network. An example of methods is described for detecting beta particles (bremsstrahlung radiation) but the proposed WNN can be applied to either the detection of positrons or gamma rays using the gamma camera.

8 Claims, 7 Drawing Sheets

OTHER PUBLICATIONS

Qian et al., "Three-structured nonlinear filter and wavelet transform for microcalcification segmentation in mommography." *Proc. of the SPIE IS&T Conference,* San Jose, CA, (Jan. 31–Feb. 4, 1993).

Galatsanos and Chin, "Digital restoration of multichannel images" *IEEE Trans. on ASSP,* vol. 37, pp. 415–421, (Mar., 1989).

Wang et al., "Solution of inverse problems in image processings by wavelet expansion" *Proceedings of the Int'l Conference on Acoustics, and Signal Proc.,* Minneapolis, MN, pp. V61–64, (Apr., 1993).

Banham et al., "Multichannel restoration of single channel images using a wavelet decomposition." *Proc. of the Int'l Conf. on Acoustics, Speech, and Signal Processing,* Minneapolis, MN, pp. V281–284, (Apr., 1993).

Kallergi et al., "Bremsstrahlung imaging with the gamma camera" *Proceedings of SPIE—The Int'l Society for Optical Engineering Conf.,* in California, (Feb., 1992).

Mallat, "Multifrequency channel decompositions of images and wavelet models" *IEEE Trans. Acoust. Speech, Signal Processing,* 37, pp. 2091–2110, (1989).

Mallat, "A theory for multiresolution signal decomposition: the wavelet representation" *IEEE Trans. Patt. Anal. Machine Intell.,* 11(7), pp. 674–693 (1989).

Vaidyanathan, "Quadrature mirror filter banks, M–band extensions and perfect–reconstruction technique" *IEEE ASSP Mag.,* 4, pp. 4–20 (Jul., 1987).

Vaidyanathan, "Theory and design of M–channel maximally decimated quadrature mirror filters with subituary M, having the perfect–Reconstruction Property." *IEEE Trans. on APPS.,* vol., 35, No. 4, pp. 476–492 (Apr., 1987).

Qian et al., "Digital mammography: m–channel quadrature mirror filters (QMFs) for microcalcification extraction" *Computerized Medical Imaging and Graphics,* 18(5) (1994).

Qian et al. "Bayesian image restoration: an application to edge–preserving surface recovery" IEEE Transactions on Pattern Analysis and machine intelligence, vol. 15, No. 7, pp. 748–752 (1993).

| | ID(cm) | ROI(cm) | $\mu_{raw}$ | $\mu_{OSNNH}$ | $\mu_{WNN}$ |
|---|---|---|---|---|---|
| "Y SOURCE | | | | | |
| LARGE SOURCE | 6.0 | 7.0 | 0.131 | 0.133 | 0.133 |
| MEDIUM SOURCE | 3.5 | 4.5 | 0.142 | 0.135 | 0.135 |

| | ID(cm) | ROI(cm) | $\mu_{raw}$ | $\mu_{OSNNH}$ | $\mu_{WNN}$ |
|---|---|---|---|---|---|
| 32P SOURCE | | | | | |
| LARGE SOURCE | 6.0 | 7.0 | 0.136 | 0.122 | 0.122 |
| MEDIUM SOURCE | 3.5 | 4.5 | 0.142 | 0.120 | 0.124 |

Fig-10

CALCULATED ATTENUATION COEFFICIENTS FOR BOTH SOURCES $^{32}P$ AND $^{90}Y$ FOR THE RAW AND RESTORED IMAGES USING THE OSNNH AND WNN FILTERS

NUCLEAR IMAGING ENHANCER

BACKGROUND OF THE INVENTION

1. Field of the Invention

The invention relates to a nuclear detector (gamma camera) for nuclear medicine imaging and the use of a wavelet based neural network (WNN) for segmenting noise from signal and the restoration of the signal using the neural network.

2. Description of the Related Art

The gamma camera system response function for single photon detection results in image degradation due to photon scattering effects or photon penetration through the collimated detector [1]. Alternatively for bremsstrahlung imaging, such as in the detection of beta particles during antibody therapy, the enhanced effects of photon scattering and high energy photon penetration through the collimated detector results in further significant image degradation [2]. The sensitivity of detection of beta particles, as opposed to single photon detection, is greatly diminished due to the poor conversion efficiency of beta particle energy to bremsstrahlung radiation and results in poor signal to noise ratio in bremsstrahlung detection[2]. Quantitative imaging of bremsstrahlung radiation, therefore, poses a very difficult problem for image restoration; namely the detection of weak signals imbedded in noise, where the Poisson noise processes includes both additive and multiplicative sources [2–3]. Similarly, the conditions for image restoration filters must be met for bremsstrahlung detection namely: the shift invariance of the point spread function (PSF), radial symmetry of the PSF and finally uniformity of the PSF with source depth [3]. These conditions have been achieved using pure beta emitters $^{32}$P[3] and $^{90}$Y[4] as reported by these investigators.

Image restoration filters have been proposed for single photon detection to partly compensate for image degradation and have met with limited success. Methods proposed have included the Weiner filter [4], the Metz filter and constrained Least Squares filters [5] that generally require an a priori knowledge of the system response function and an estimate of the noise power spectrum. These filters generally involve two components, a low pass filter for noise suppression and an inverse filter for deconvolution. These filters have had limited success because the inverse operation often makes the restoration an ill conditioned, unstable, or singular problem. When the Weiner filter is applied to bremsstrahlung images, the combined influence of the degraded system response and high noise content introduces greater instability in the deconvolution that results in ringing artifacts and an over compensation of the system response function [5, 6]. These ringing artifacts and restoration instability are particularly noticeable for images of isolated sources used to calibrate the gamma camera for quantitative measurements as proposed in this work [7]. Alternative methods for image restoration are therefore necessary for imaging of beta emitters using the gamma camera for either the planar or tomographic detection modes. Similar alternative methods are required for imaging of single photon emitters (gamma rays) or positrons using the gamma camera in either the planar or tomographic detector modes.

The prior art proposed the use of a novel order statistic neural network hybrid (OSNNH) filter for image restoration for bremsstrahlung detection [6]. The order statistic filter was used for noise suppression for the first stage, cascaded with the neural network (NN) for deconvolution. Order statistic filters have been shown to provide a more robust performance than linear filters or modification to median filters for noise suppression [7] and performed well for noise suppression in bremsstrahlung imaging [6]. The NN system for deconvolution that includes a knowledge of the system response function, in turn, avoided the serious problem of the inverse filter, since for this algorithm no matrices are inverted, as previously reported [8–10]. The OSNNH filter, however, may not have optimum performance for all image noise levels. Furthermore, it is computationally intensive and the overall filter architecture is not optimum for either parallel processing or very large system integration (VLSI) implementation as required for planar or SPECT modes of detection for the gamma camera.

For the above cited and other related articles, see the references listed at the end of the specification.

SUMMARY OF THE INVENTION

The invention includes a method of detecting a nuclear image and segmenting noise from the detected image as opposed to use of noise suppression filters. The method includes the steps of: detecting a nuclear image; storing the image; decomposing the image based on wavelet transform into a plurality of subimages of different resolution to concentrate image noise in at least one of the subimages and to concentrate the image signal in another of the subimages; selecting dominant subimages based on resolution representative of the nuclear image to eliminate the concentrated noise subimage; restoring the selected dominant subimages to a restored image of improved resolution by a neural network; and reconstructing the selected dominant subimages to a single high resolution image signal.

The subject invention provides an alternative approach to the prior art by using a multiresolution wavelet-based neural network (WNN) for image restoration that is computationally more efficient and provides an improved basis for noise removal and related ringing artifact reduction for nuclear imaging using the gamma camera. The principle of multichannel wavelet-based methods is that they may exploit the interdependence between channels in a signal which has more than one band of related information [11–22].

The subject invention uses multiresolution decomposition of the nuclear image into different subimages to isolate signal from noise, followed by a modified neural network architecture specifically for multichannel image restoration selectively applied to the dominant reconstructed subimages of the signal. An M-channel wavelet transform differentiates signal from noise based on their dominant features that are located in different resolution and frequency channels. An additional correlation criteria provides a more quantitative basis for differentiation of signal from noise. The NN model avoids the common inverse problem associated with other image restoration filters such as the Weiner filter. The relative performance of the WNN, for M=2 channel, has been compared to a previously reported order statistic neural network hybrid (OSNNH) filter using simulated degraded images with different noise levels. Quantitative measurements such as the normalized mean square error (NMSE) and signal to noise ratio (SNR) were used to compared filter performance. The WNN yielded comparable results for image restoration with suggested better performance for the images with higher noise levels as often encountered in bremsstrahlung detection. For example, attenuation measurements were preformed for bremsstrahlung detection using two radionuclides, $^{32}$P and $^{90}$Y. Similar values for attenuation were observed for the OSNNF and WNN filters. However, for sources in high background activity or high noise content, the WNN performed better than the OSNNF, particularly if M≧2 channels are used. More importantly, the WNN was computationally more efficient by a factor of 4–6 compared to the OSNNH filter. The filter architecture is also more optimum for parallel processing or VLSI implementation as required for planar and particularly for SPECT mode detection. The WNN should also be useful in quantitative imaging of single photon emitters or positron emitters.

FIGURES IN THE DRAWINGS

Other advantages of the present invention will be readily appreciated as the same becomes better understood by reference to the following detailed description when considered in connection with the accompanying drawings wherein:

FIGS. 8(a)–(f) are images of the spherical source (3.5 cm diameter) at 10 cm depth in the water tank for two beta emitters ($^{32}P$ and $^{90}Y$) using bremsstrahlung detection. Top: $^{32}P$: (a) unprocessed data, (b) restored data by OSNNH filter, (c) restored data by WNN filter. Bottom: $^{90}Y$: (d) unprocessed data (e) restored by OSNNH filter (f) restored by WNN filter;

DESCRIPTION OF THE PREFERRED EMBODIMENT

Figure 1:
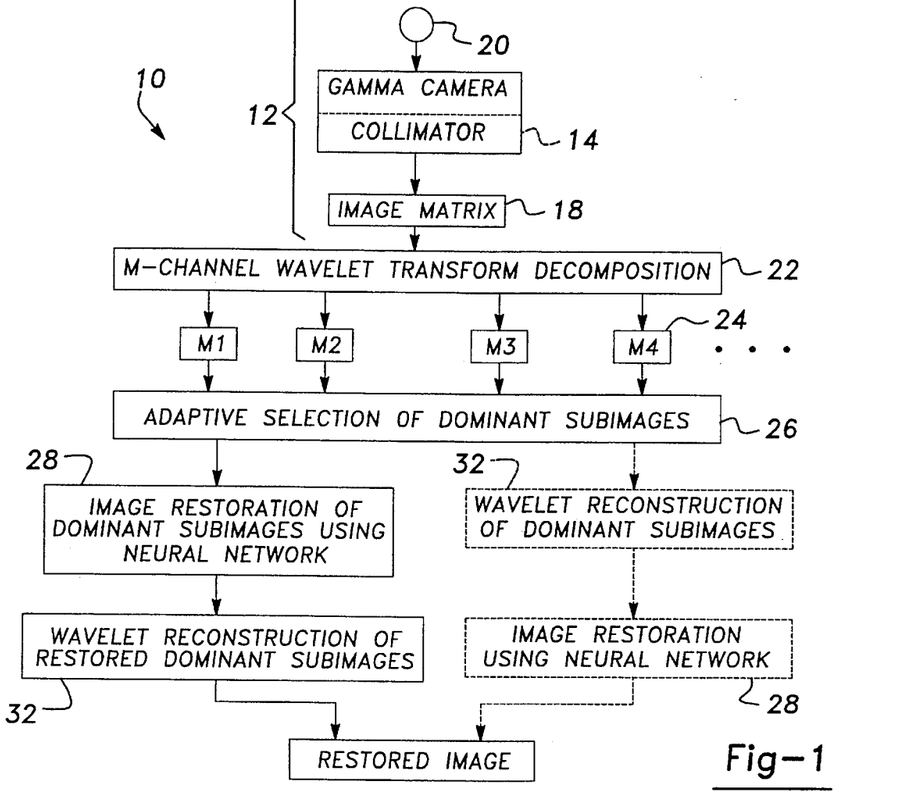
FIG. 1 is a block diagram of the subject invention as used with a camera.

A filter assembly 10 is illustrated in FIG. 1. The filter assembly 10 is used in conjunction with a nuclear detector 12 to minimize or remove noise from a detected nuclear image signal to allow restoration of the detected signal. The nuclear detector 12 may include a gamma camera, single photon emission computed tomography (SPECT) system, or other nuclear detector type. The preferred embodiment utilizes a gamma camera as its example; however, it is to be understood by those skilled in the art that any other type of nuclear detector may be utilized.

The gamma camera 12 includes a collimator 14 that collimetes the bremsstrahlung or gamma rays to form an image matrix 18 of the object 20 in electronic form forming an image signal. The filter assembly 10 receives the image from the matrix 18 to process the signal and remove noise therefrom producing a restored image formed of dominant subimages of the original detected signal and of increased resolution.

The filter assembly 10 includes decomposition means 22 for receiving the nuclear image from the matrix 18 and for decomposing the nuclear image based on multichannel wavelet transform to produce different subimages which isolate the signal of the image from noise. The decomposition means 22 decomposes the image into M-channel subimages 24 based on frequency and resolution.

Selecting means 26 selects the dominant subimages from the M-channel subimages 24 based on frequency and scale (resolution). This eliminates the subimages containing substantially noise. The M-channel wavelet transform differentiates the image signal from noise based on their dominant features that are located in different resolution and frequency channels.

Figure 3:
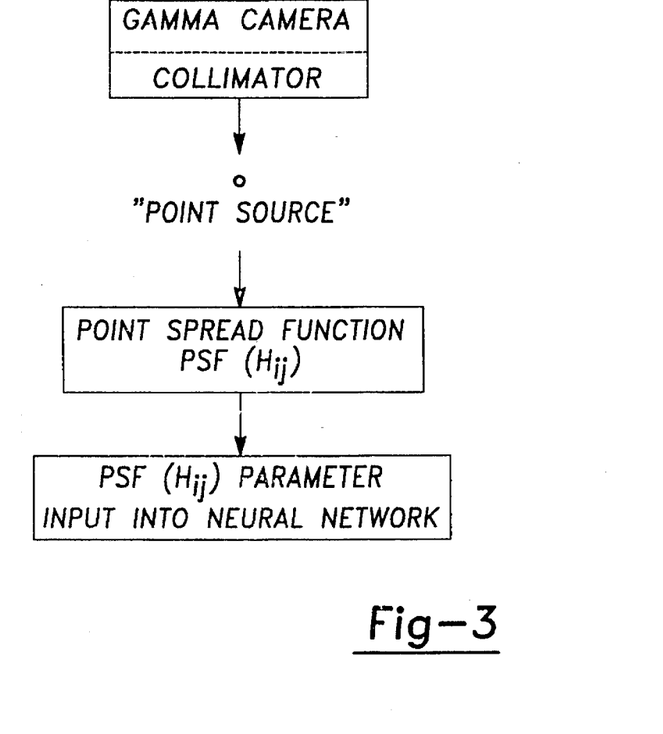
FIG. 3 shows a block diagram of measurement of the point spread function and input in the neural network.
Figure 4:
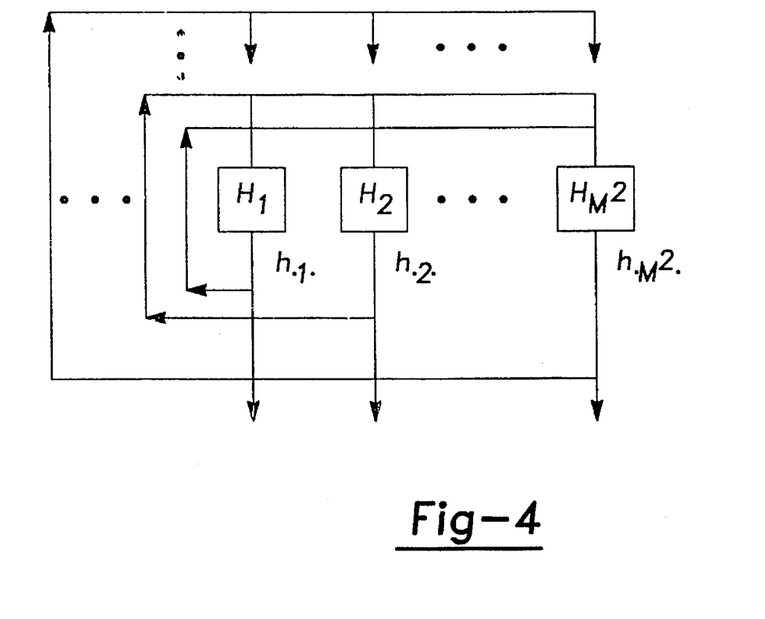
FIG. 4 is the general diagram of the multichannel neural network for image restoration, in which $H_1, H_2 \ldots H_{M2}$ are represented neural networks in different channels.

The filter 10 also includes restoration means 28 which restores the selected dominant subimages using a neural network based on the physically measured point source response function of the detector or camera 12 as measured in FIG. 3. Reconstructing means 32 reconstructs the multiple subimages based on wavelet transformation producing a high resolution nuclear image that improves image contrast or the ability to detect the signal of interest (radiation source). The order of the restoration means 28 and reconstruction means 32 may be reversed. For example, the preferred embodiment illustrates that each dominant subimage is restored and then all restored subimages are reconstructed into a single image. However, it to be understood that the subimages may be first reconstructed into a single image and then the single image restored based on the teachings herein.

Multiresolution formulation for image restoration is based on both wavelet-based multiresolution (multichannel) decomposition and multichannel image processing techniques. The multiresolution decomposition may be obtained by wavelet expansion. Wavelet orthonormal bases have been constructed and studied extensively from both a mathematical and a signal processing point of view. The orthogonal wavelets obtained by Debauchees were used, by way of example, for the development of this technique. Processing of multichannel images is substantially different from that of single-channel images. Although there is large amount of work in the literature on digital restoration of single-channel images [12–13], there has been little investigation of multichannel restoration [14–15]. The extension of existing single-channel image restoration techniques to multichannel restoration is a nontrivial and difficult task. Filters that are optimal for single-channel images may be suboptimal when applied individually to the separate channels of multichannel images.

DECOMPOSITION MEAN 22:

The following describes the function and algorithms forming the decomposition means 22.

General Case for M-Channel Wavelet Filter Bank:

Multiresolution formulation is an extension of two-band wavelet filters introduced by Debauchees [17] and Mallat [18, 19] for the decomposition of a signal into components at multiple scales, which have been generalized to produce M-band wavelet filters. An M-band wavelet filter bank splits a signal into M bands, yielding multiple scales as well as multiple frequencies of the signal. The basis function of a discrete M-band wavelet transform can be expressed as follows;

$$\psi_{m,n}(x) = M^{-m/2}\psi_{m,n}(M^{-m}x-n), n, m \in Z \qquad (1)$$

where Z is the set of integers. When subjected to the functional operations of shifts and dyadic dilation, $\psi$ yields an orthogonal basis of $L^2(R)$ which is the vector (Hilbert) space of measurable square-integrable functions [18]. The functions of Eq.(1) form a complete orthonormal system for $L^2(R)$, which is given as follows:

$$L^2(R) = \ldots \oplus W_{-2} \oplus W_{-1} \oplus W_0 \oplus W_1 \oplus W_2 \oplus \qquad (2)$$

where $W_i$ is the wavelet subspace spanned by $\{\psi_{m,n}(X)\}_{n=-\infty}^{n=+\infty}$.

The general case for M-channel wavelet filter bank can be generated from wavelets by using an extension of the multiresolution analysis of Mallat [20,21]. The starting point is a scaling function $\Phi(x)$ which satisfies the M-scale difference equation $$\Phi(x) = \sqrt{M} \sum_k h_0(k)\Phi(Mx-k) \qquad (3)$$

The coefficients $h_0(k)$ in Eq. (3) have to meet several conditions for the set of basis wavelet functions in Eq.(1), namely: uniqueness, orthonormal and with a certain degree of regularity [19,21].

The dilations and translations of the scaling function induce a multiresolution analysis of $L^2(R)$, a nested chain of closed subspaces of $L^2(R)$ ($\ldots \subset V_{-1} \subset V_0 \subset V_1 \subset V_2 \ldots$) such that $$V_{-\infty} = \{0\}, V_\infty = L^2(R) \qquad (4)$$

where $V_i$ is the subspace spanned by $\{\Phi_{m,n}(x)\}_{n=-\infty}^{n=+\infty}$, and $V_i$ and $W_i$ are related by:

$$V_i \oplus W_i = V_{i+1} \qquad (5)$$

which extends to $$V_i \oplus W_i \oplus W_{i+1} = V_{i+2} \qquad (6)$$

The current published work usually involves the use of M=2 [17]. If $V_j$ denotes the $L_2(R)$ closure of the span of the function $\Phi(M^j x-k)$, $k \in Z$, then the wavelet space $W_j = V_{j+1} \ominus V_j$ is the span of $\psi_i(M^j x-k)$ where $$\psi_i(x) = \sqrt{M} \sum_k h_i(k)\Phi(Mx-k) \qquad (7)$$

where $h_i(k), i \in \{1, \ldots, M-1\}$, is an M-channel filter bank. If $\Phi$ is assumed to have orthonormal shift then the M-channel filter bank satisfy $$\sum_n h_i(n)h_j(n-Ml) = \delta(i-j)\delta(l) \qquad (8)$$

In the digital signal processing domain [19], $h_i(k), i \in \{1, \ldots, M-1\}$, are called Quadrature Mirror Filter (QMF) bank. The coefficients $h_i(k)$ play a very crucial role in a given wavelet transform. The implementation of a wavelet transform does not require the explicit forms of $\Phi(x)$ and $\psi(x)$ but only depends on $h_i(k), i \in \{1, \ldots, M-1\}$.

Formulation: Orthonormality of the wavelet basis implies the uniqueness of the filter bank associated with the scaling and wavelet filters. This means the set of functions $\{\Phi_{m,n}(x)\}$ and $\{\psi_{m,n}(x)\}$ form an M-band wavelet tight frame for $L^2(R)$.

That is, for all signals $f(t) \in L^2(R)$:

$$f(x) = \sum_n \langle f, \Phi_n(x) \rangle \Phi_n(x) + \sum_{m,n} \langle f, \psi_{m,n}(x) \rangle \psi_{m,n}(x) \qquad (9)$$

Suppose $f(x) \in V_M$, and if we use $A_m$ and $B_m$ as a corresponding "approximation operator" (9), $f(x)$ can be expressed as:

$$f(x) = A_0 f(x) + \sum_m B_m f(x) \qquad (10)$$

Two-dimensional Wavelets: In order to apply wavelet decompositions to gamma camera images, two-dimensional extensions of wavelets are required. An efficient way to construct this is to use "separable wavelets" obtained from products of one-dimensional wavelets and scaling functions [18],[19]. The two dimensional functions can be constructed as:

$$\Phi(x,y) = \Phi(x)\Phi(y)$$

$$\psi(x,y) = \psi(x)\Phi(y)$$

$$\psi(x,y) = \psi(x)\psi(y) \qquad (11)$$

The functions of (11) correspond to the separable two-dimensional filter banks. Without loss of generality, if the resolution level is M+1, the basis functions for $f(x,y) \in V_{M+1}$ and $W_j$ (j=M, M-1, ..., 1) can be ordered by $$\Phi_M(x)\Phi_M(y), \Phi_M(x)\psi_M(y), \ldots, \Phi_M(x)\psi_2(y), \Phi_M(x)\psi_1(y)$$

$$\psi_M(x)\Phi_M(y), \psi_M(x)\psi M(y), \ldots, \psi_M(x)\psi_2(y), \psi_M(x)\psi_1(y)$$

$$\psi_{M-1}(x)\Phi_M(y), \psi_{M-1}(x)\psi_M(y), \ldots, \psi_{M-1}(x)\psi_2(y),$$

$$\psi_{M-1}(x)\psi_1(y)$$

$$\ldots$$

$$\ldots$$

$$\ldots$$

$$\psi_1(x)\Phi_M(y), \psi_1(x)\psi_M(y), \ldots, \psi_1(x)\psi_2(y), \psi_1(x)\psi_1(y) \qquad (12)$$

Corresponding to the matrix of the basis functions, (10) can be represented by the following block-matrix:

$$A_{Mx}f(x,y)A_{My}f(x,y), A_{Mx}f(x,y)B_{My}f(x,y), \ldots,$$

$$A_{Mx}f(x,y)B_{2y}f(x,y), A_{Mx}f(x,y)B_{1y}f(x,y)$$

$$B_{Mx}f(x,y)A_{My}f(x,y), B_{Mx}f(x,y)B_{My}f(x,y), \ldots,$$

$$B_{Mx}f(x,y)B_{2y}f(x,y), B_{Mxf(x,y)B1y}f(x,y)$$

$$B_{Mx-1}f(x,y)A_{My}f(x,y), B_{Mx-1}f(x,y)B_{My}f(x,y), \ldots,$$

$$B_{Mx-1}f(x,y)B_{2y}f(x,y), B_{Mx-1}f(x,y)B_{1y}f(x,y)$$

$$\ldots$$

$$\ldots$$

$$\ldots$$

$$B_{1x}f(x,y)A_{My}f(x,y), B_{1x}f(x,y)B_{My}f(x,y), \ldots,$$

$$B_{1x}f(x,y)B_{2y}f(x,y), B_{1x}f(x,y)B_{1y}f(x,y) \qquad (13)$$

The wavelet representation of the operator described above has interesting interpretations. First, the representation means that the 2-D image is decomposed into $M^2$-channel subimages, which allows the multichannel image processing techniques to be used. Second, in the above wavelet-based image compression, $A_{Mx}f(x,y)A_{My}f(x,y)$ is the "low-frequency" portion of the operator while other blocks in Eq.(13) are "high-frequency" components of the operator. This motivates a general and consistent scheme for "scaling down" from a fine to a coarse grid.

SELECTION MEANS 26:

The wavelet-based neural network 28 itself removes the noise while restoring the image. Since the energy of most nuclear images concentrates in relatively low frequencies/resolutions, and the energy of Poisson noise is normally distributed in high frequencies/resolutions, the SNR is lower in high frequencies/high resolutions and higher in lower frequencies/resolutions. In such cases, it is better to remove some high resolution data (remove the noise) and perform the restoration only in low resolutions. The sharp edges in the image also appear in high frequencies/high resolutions.

In order to identify whether noise or image details in a certain high frequency/resolution channel, a gauge function is constructed as a criterion to locate dominant frequency/resolution channels. For example, an $L_p$-norm followed by multichannel correlation is proposed as a gauge function for the measurement. The commonly used $L_p$-norm function is expressed as $[\iint_\Omega |f(x,y)|^p \, dxdy]^{1/p}$, and the multichannel correlation was estimated. In the calculation of the gauge function value of each decomposed image, if the value of a subimage is significantly smaller than others, this subimage is considered noise and its abandoned. The image deconvolution by neural network is only implemented in dominant subimages (dominant frequency/resolution channels). The significance of this method is that noise removal is computationally simple, which is different from common techniques [3,4,8,11,12], particularly for images having very high noise content, such as in bremsstrahlung imaging single photon detection or positron detection in medical nuclear imaging. Most alternative techniques for noise removal are computationally intensive.

RESTORATION MEANS 28:

The neural network 28 proposed for the restoration problem is based on optimization network. The primary computational goal in the network model is to optimize a given energy function. The model is designed to freely exploit a tailored training criteria to best satisfy the specific application requirements. The objective of the neural network is to find the optimal weights to minimize the error function established for image restoration as previously reported by [8–11]. For a nuclear detector such as the gamma camera, the blurred image F can be modeled by the sum of the operation of the 2-dimensional blur matrix M on the object X and the statistical noise n:

$$F = HX + n \quad (14)$$

where F, X, and n are lexicographic orders, by either column or row, of the two-dimensional image of size N×N into one-dimensional vectors of length $N^2$. The matrix H is the discrete representation of the degradation of dimension $N^2 \times N^2$.

The wavelet decomposition of the nuclear medicine imaging system represents a multichannel imaging system with $M^2$ channels, the imaging model of Eq.(14) becomes $$F_i = \bar{H}_i X_i + n_i \text{ for } i=1,2,\ldots,M^2 \quad (15)$$

where $F_i$, $X_i$, $n_i$ and $\bar{H}_i$ are the observed subimage, the ideal subimage, the noise, and the degradation function corresponding to ith channel, respectively, where $\bar{H}_i = [H_{i1}, H_{i2}, \ldots, H_{i(M \times M)}]$, the $H_{ij}$ ($i \neq j$; $j=1,2,\ldots,M^2$) represents the cross-channel degradation between channels i and j. Each subband signal is decimated by the factor of M. The subimage is then the size L×L where (L=N/M).

Objective Function for Optimization: The multichannel restoration problem can be formulated as a constrained least-squares problem which can then be formulated so that it minimizes $\|F_i - \bar{H}_i X_i\|^2$ subject to the factor $\|D_i X_i\|^2$ $$E = \sum_{i=1}^{M^2} \|F_i - \bar{H}_i X_i\|^2 + \lambda_i \|D_i X_i\|^2 \quad (16)$$

for $i = 1, 2, \ldots, M^2$ where $\lambda_i$ is control parameter and $D_i$ is two-dimensional linear operator. Equation (16) allows the neural network to have additional control over the restoration process [7].

The parameter $\lambda_i$ in Eq. (16) is used to obtain a balance between image restoration and filter stability. The coefficient i corresponds to the different channels described above. The processed images would be overrestored and the filter would be unstable if $\lambda_i$ was too small and the converse would be true if $\lambda_i$ was too large. Different values of $\lambda_i$ ranging from 0.0001 to 0.5 were empirically evaluated, based on the filter performance for the simulated images and experimentally acquired images. For the work reported here, this parameter was set equal to 0.5, the same as that previously reported for the OSNNF filter [7], and fixed for all results presented in this work for the simulated phantom and patient images and for both P-32 and Y-90, i.e., same degree of restoration for both isotopes ($\lambda=0.5$).

The neural network uses adaptive Fuzzylogic rule for image restoration. The adaptive neural network with Fuzzylogic rule is based on the formulation of the restoration problem as one of minimizing an error function with constraints. The error function is to seek a decovolution approximation in a least squares sense. Meanwhile, the constraints term is a smoothness to balance the noise suppression and ringing reduction. There is a parameter called regularizer which determines the relative importance between the error function and constraints. The restoration is operated by using the spontaneous energy minimization process of the neural network. The image restoration error, such as the ring effects and noise overriding, is caused by two counter productive phenomena with the variation of regulizer parameters. Near image edge areas, the regulizer dominates the noise magnification error. In consequence, the regularizer parameter should be adjusted to be smaller in image edge areas. While in the smooth areas, a large value of regulizer parameter should be used to reduce the noise magnification error. Trying to distinguish between smooth and edge information in the image is an inherently ambiguous problem and naturally leads to development of Fuzzylogicrules for choosing different regulizer parameter values. These rules may come from human experts or be generated automatically by matching input output pairs through a training routine. We automatically generate the fuzzy rules to train the membership function by using an LMS (least mean squares) algorithm. This membership function allows us to describe the "big difference" and the "small difference" between gray levels. The training process is divided into three steps. First, assume the initial values of the membership function form a triangle function. The initial value IIk(0) is stored in a K+1 array. Second, use the original image to update IIk(1) at iteration 1. Continue the process until it converges. Finally, fit the trained data to the IIfunction to get the regulizer parameter.

Neural Network Architecture: The neural network designed for image restoration using the gamma camera in [7] can be modified for the multichannel image restoration minimizing the equation of (17). The image gray-level function can be represented by a simple summation over the neuron's state variables, i.e., $X_j = \Sigma_1^T V_{j1}$[7]. The dynamics of the neural network for each single channel can then be described by the following system of non-linear differential equations:

$$C_{ip} \frac{du_{ip}}{dt} = \sum_{j=1}^{L^2} \sum_{l=1}^{T} D_{ipj} V_{jpl} - \sum_{j=1}^{L^2} h_{jip} f(S_{jp}(V)) - \frac{u_{ip}}{D_{ip}} \qquad (17)$$

where $C_{ip}$ is the capacitance of neuron i in p-channel (p=1,2 ..., $M^2$), L (L=N/M) is the size of subimage, and the amplifiers in a certain channel are functions of:

$$S_{jp}(V) = \sum_k^{L^2} h_{jpk} x_{kp} - f_{jp} = \sum_k^{L^2} \sum_l^T h_{jpk} V_{kpl} - f_{jp} \qquad (18)$$

The system in Eq. (17) for each different p (p=1,2, ... $M^2$) has proved in [6] that it has only a finite number of "equilibrium points" and all nonequilibrium solutions of Eq. (17) for each p tend to an equilibrium point as $t \to +\infty$. Therefore, the neural network for each p acts to minimize the mean square error function which solves the restoration problem in each channel. In order to obtain multichannel image restoration, the neural network will attempt to minimize the mean square error function and find a potential solution to the restoration problem in all channels as follows:

$$\xi = \frac{1}{2} \sum_{p=1}^{M^2} \sum_{i=1}^{L^2} \left( f_{ip} - \sum_{j=1}^{L^2} \sum_{l=1}^{T} h_{ipj} V_{ipl} \right)^2 - \qquad (19)$$

$$\sum_{p=1}^{M^2} \sum_{i=1}^{L^2} \left( \sum_{j=1}^{L^2} D_{ipj} \sum_{l=1}^{T} V_{jlp} \right)^2 =$$

$$\frac{1}{2} \sum_{p=1}^{M^2} \|F_p - \overline{H}_p X_p\|^2 + \|D_p X_p\|^2$$

Equations (15–19) can be further simplified by using the following notation;

$$F = \begin{bmatrix} F_1 \\ F_2 \\ \cdot \\ \cdot \\ \cdot \\ F_{M^2} \end{bmatrix} \quad X = \begin{bmatrix} x_1 \\ x_2 \\ \cdot \\ \cdot \\ \cdot \\ x_{M^2} \end{bmatrix} \quad n = \begin{bmatrix} n_1 \\ n_2 \\ \cdot \\ \cdot \\ \cdot \\ n_{M^2} \end{bmatrix} \qquad (20)$$

where F, X and n are $N^2 = L^2 M^2$ in length. The degradation H of the multichannel image is $$H = \begin{bmatrix} H_{11} & H_{12} & \cdots & H_{1M^2} \\ H_{21} & H_{22} & \cdots & H_{2M^2} \\ \cdot & \cdot & \cdots & \cdot \\ \cdot & \cdot & \cdots & \cdot \\ \cdot & \cdot & \cdots & \cdot \\ H_{M^21} & H_{M^22} & \cdots & H_{M^2M^2} \end{bmatrix} \qquad (21)$$

and is of dimension $N^2 \times N^2$. Finally, the multichannel imaging equation can be written as $$F = HX + n \qquad (22)$$

The neural network for the multichannel image restoration problem as expressed in Eqs.(17) and (19) obtains the linear minimum mean square error (LMMSE) solution to Eq. (22). The minimizer of the LMMSE solution to Eq. (22) can be expressed as:

$$X = R_x H^T [H R_f H^T + R_n]^{-1} F \qquad (23)$$

where $R_f$ and $R_n$ are the autocorrelation of the multichannel signal and noise, respectively. Using the definitions $R_x^{ij} = E[x_i x_j^T]$ and $R_n^{ij} = E[n_i n_j^T]$, we have:

$$R_x = \begin{bmatrix} R_x^{11} & R_x^{12} & \cdots & R_x^{1M^2} \\ R_x^{21} & R_x^{22} & \cdots & R_x^{2M^2} \\ \cdot & \cdot & \cdots & \cdot \\ \cdot & \cdot & \cdots & \cdot \\ \cdot & \cdot & \cdots & \cdot \\ R_x^{M^21} & R_x^{M^22} & \cdots & R_x^{M^2M^2} \end{bmatrix} \qquad (24)$$

$$R_n = \begin{bmatrix} R_n^{11} & 0 & \cdots & 0 \\ 0 & R_n^{22} & \cdots & 0 \\ \cdot & \cdot & \cdots & \cdot \\ \cdot & \cdot & \cdots & \cdot \\ \cdot & \cdot & \cdots & \cdot \\ 0 & 0 & \cdots & R_n^{M^2M^2} \end{bmatrix}$$

The matrice $R_x$ and $R_n$ are of dimension $NM^2 \times NM^2$. The solution of Eq.(23) requires the inversion of $[H R_f H^T + R_n]$. From the computation view for any realistic application, for a simple example with N=128 and M=3, the direct computation of Eq.(23) is not practical, requiring the inversion of a 147456×147456 matrix. Although the simplification can, to some extent, be obtained by introducing block-Toeplitz to block-circulant approximation using DFT makes the computation of Eq.(23) available, the algorithm such as Wiener filter creates ring effects caused by the ill-conditioned blur matrix and noise overriding caused by matrix inversion. In consequence, wavelet-based neural network is designed for obtaining linear minimum mean square error (LMMSE) solution to Eq.(22), which avoids the problems associated with the inverse operation.

The Dynamics of the Neural Network: The dynamics of the neural network processing element is given by $$x_i^{new} = \begin{cases} 1 & \text{if } \sum_{j=1}^{n} h_{ij} x_i^{old} > T_i \\ x_i^{old} & \text{if } \sum_{j=1}^{n} h_{ij} x_i^{old} = T_i \\ -1 & \text{if } \sum_{j=1}^{n} h_{ij} x_i^{old} < T_i \end{cases} \qquad (25)$$

The processing elements of the network are updated one at a time. The subsequent movement of the network's state vector $x = (x_1, x_2, \ldots, x_N)^T$ on cube $\{-1, 1\}^N$ which is defined as:

$$\{-1,1\}^N = \{x = (x_1, x_2, \ldots, x_N) \in R^N | x_i \in \{-1,1\}, \text{ for all } 1 \leq i \leq N\} \qquad (26)$$

Equation (26) is referred to as a bipolar cube in N-dimensional Euclidean geometry. Many neural networks have processing elements with output signals in the discrete set $\{-1,1\}$. Each processing element has such a plane; when the state of a processing element is being updated, if the current state x of the network (in other words, the vertex of the cube that the network is currently located at) lies on the "plus" side of this plane, then the new output of the processing element will be +1; if x lies on the "minus" side of the hyperplane, then the new output will be −1. Finally, if the state happens to lies on this plane, then the processing element's state remains unchanged. If any of the N planes go through one or more of the vertices of the $\{-1,1\}^N$ cube, then one can tilt or move these planes so as to avoid these vertices. Thus, if we adopt the convention that none of the N hyperplanes would be allowed to contain any of the $2^N$ vertices of the cube $\{-1,1\}^N$, then we could re-express the updating law for the neural network as $$x_i^{new} = \text{sgn}\left(\sum_{i=1}^{N} h_{i,j} x_i^{old} - T_j\right) \quad (27)$$

where $$\text{sgn}(u) = \begin{array}{l} +1 \quad \text{if } u \geq 0 \\ -1 \quad \text{if } u < 0 \end{array} \quad (28)$$

Figure 5:
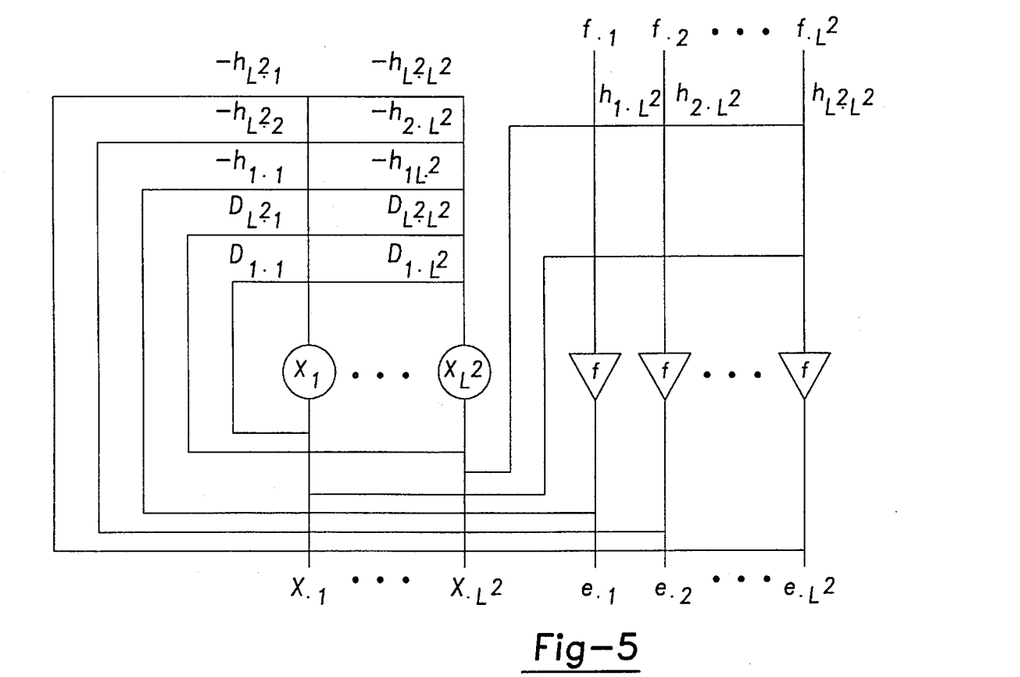
FIG. 5 is a block diagram of one of the multichannel neural networks.

The initial bipolar values of the processing element states (that is, the initial values of $x_1^{old}, x_2^{old} \ldots x_N^{old}$) are brought in on the input line, as shown in FIG. 5. These inputs and their associated weights are actually part of the internal structure of the neural network processing elements. The behavior of the neural network shown in FIG. 5 can be characterized by means of an energy function which is:

$$E(x) = \sum_{p=1}^{M^2} \sum_{i=1}^{L^2} \left(f_{ip} - \sum_{j=1}^{L^2} h_{ipj} x_{ip}\right)^2 - \quad (29)$$

$$\sum_{p=1}^{M^2} \sum_{i=1}^{L^2} \left(\sum_{j=1}^{L^2} D_{ipj} x_{ip}\right)^2$$

$$= -\sum_{p=1}^{M^2} \sum_{i=1}^{L^2} \sum_{j=1}^{L^2} w_{ipj} x_{ip} x_{jp} + 2 \sum_{p=1}^{M^2} \sum_{i=1}^{L^2} T_i x_{ip}$$

When the state of any processing element changes from +1 to −1, or vice versa, the change in energy $\Delta E$ is then:

$$\Delta E = E(x^{new}) - E(x^{old}) = -\sum_{p=1}^{M^2} \sum_{i=1}^{L^2} \sum_{j=1}^{L^2} w_{ipj} x_{ip}^{new} x_{jp}^{new} + \quad (30)$$

$$2\sum_{p=1}^{M^2} \sum_{i=1}^{L^2} T_{ip} x_{ip}^{new} + \sum_{p=1}^{M^2} \sum_{i=1}^{L^2} \sum_{j=1}^{L^2} w_{ipj} + 2\sum_{p=1}^{M^2} \sum_{i=1}^{L^2} T_{ip} x_{ip}^{old} =$$

$$2(x_{ip}^{old} - x_{ip}^{new}) \left[\sum_{p=1}^{M^2} \sum_{j=1}^{L^2} w_{kpj}\right]$$

The above result is obtained based on that, except for the $k^{th}$ processing element state $x_{kp}$, none of the other states have changed. If $x_{kp}$ has changed from −1 to +1, then $\sum_{p=1}^{M \times M} \sum_{j=1}^{L \times L} w_{kpj} x_{jp}^{old} - T_{kp}$ must have been positive and, since $x_{jp}^{old} - x_{jp}^{new} = -2$ in this case, $\Delta E$ will be negative. Similarly, if $x_{kp}$ has changed from +1 to −1 then $\sum_{p=1}^{M \times M} \sum_{j=1}^{L \times L} w_{kpj} x_{jp}^{old} - T_{kp}$ must have been negative and since $x_{jp}^{old} - x_{jp}^{new} = +2$ in this case, $\Delta E$ will be negative. If $x_{kp}$ has not changed, then $(x_{jp}^{old} - x_{jp}^{new}) = 0$ in which case $\Delta E$ will be 0. Thus, $\Delta E \leq 0$.

The wavelet-based neural network model using a dynamic algorithm to optimize the given energy function of Eq.(29) freely exploits a tailored training criteria best satisfy the solution to the specific restoration problem.

RECONSTRUCTION MEANS 32:

Reconstruction occurs in the same manner, though inverse, as the decomposition. Such reconstruction is disclosed in the prior art. Restoration by other investigators is illustrated in references [4, 5] using a gamma camera. Theory of wavelets used in general sense in reference [19, 21] modified for the problem of nuclear restoration by applicant.

Figure 2:
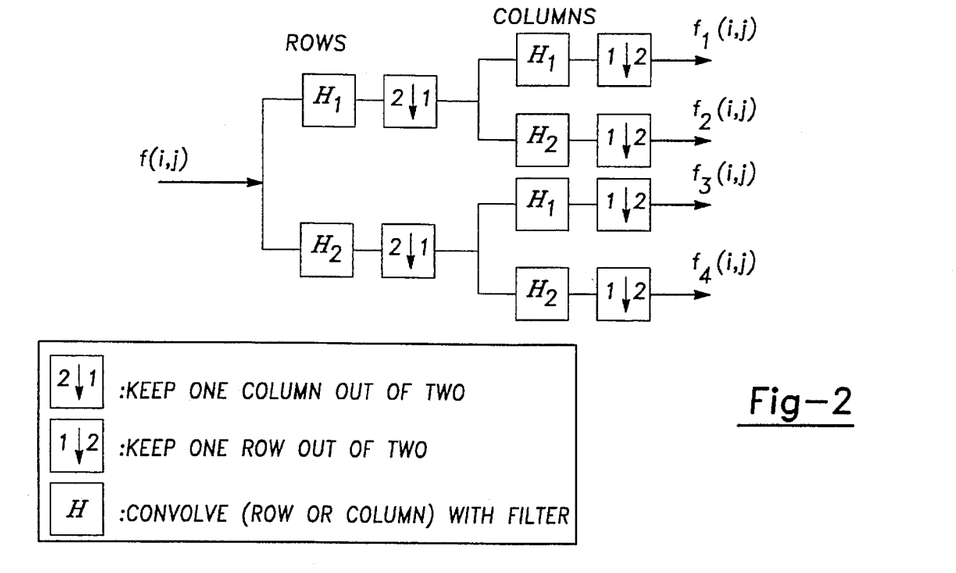
FIG. 2 is a block diagram of a two-channel tree structured wavelet transform for image decomposition.
Figure 6:
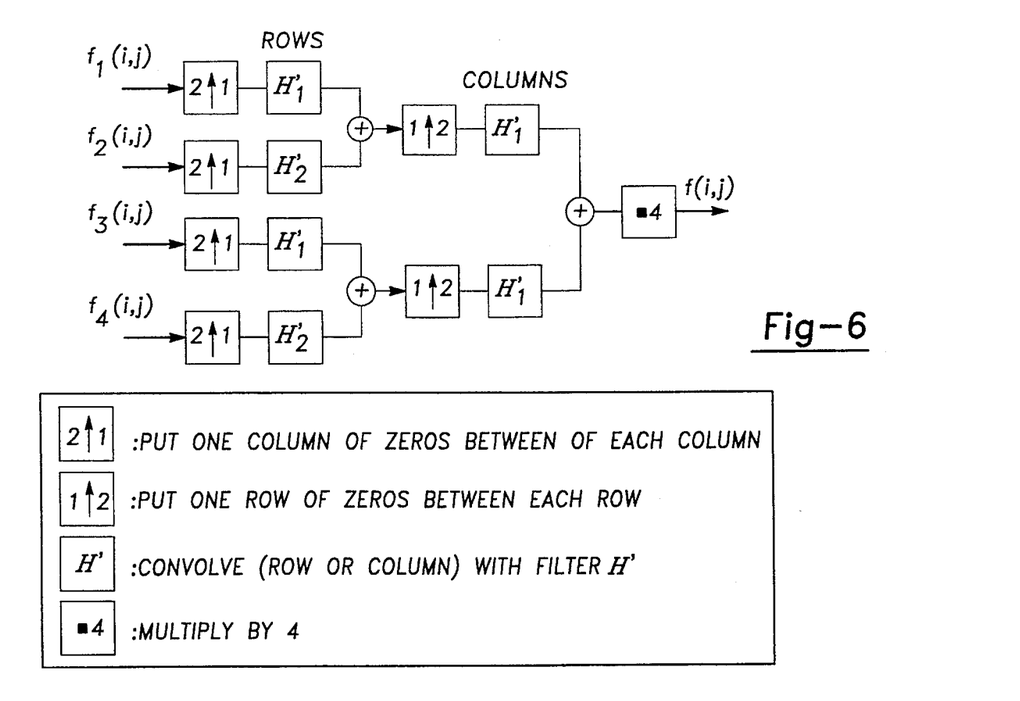
FIG. 6 is a block diagram of a two-channel, tree structured wavelet transform for image reconstruction.
Figure 7A:
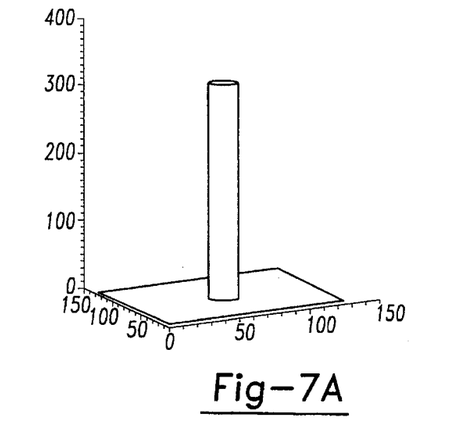
FIGS. 7(a)–(f) are simulation studies using the subject invention: (a) the simulated image of one cylindrical source, (b) the system point source response called point spread function (PSF), (c) the blurred image degraded by the PSF and higher level noise, (d) decomposition of the image using two channel wavelet transform, (e) restoration result using OSNNH filter, (f) restoration result using WNN.
Figure 7B:
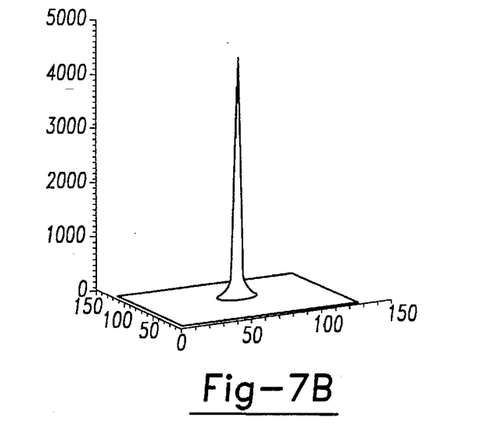
Figure 7C:
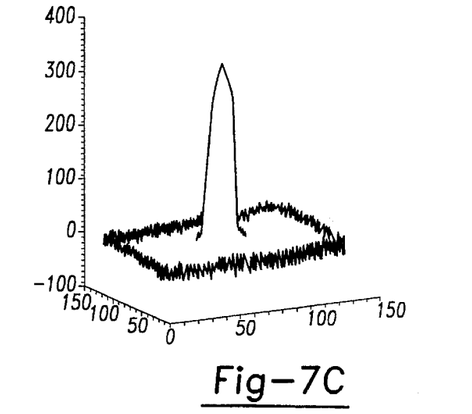
Figure 7D:
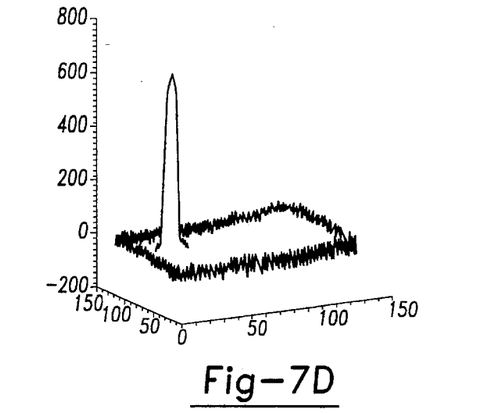
Figure 7E:
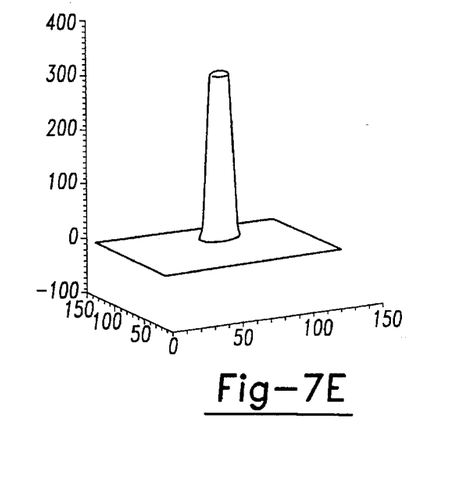
Figure 7F:
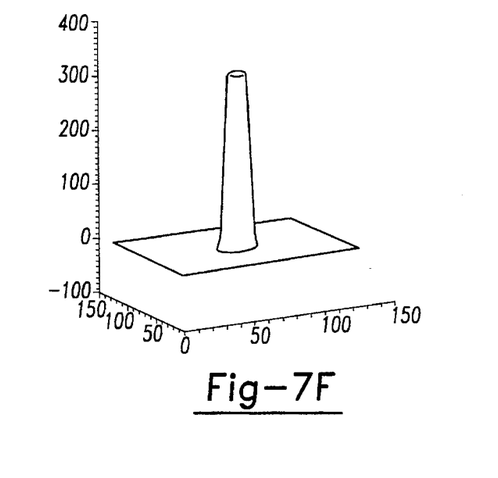
Figure 8A:
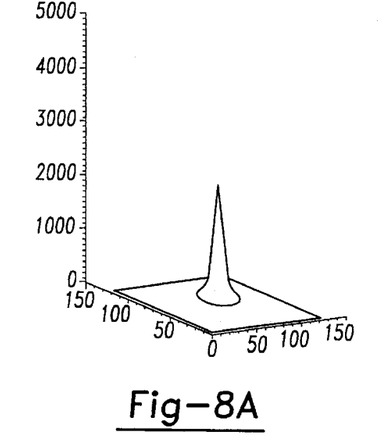
Figure 8B:
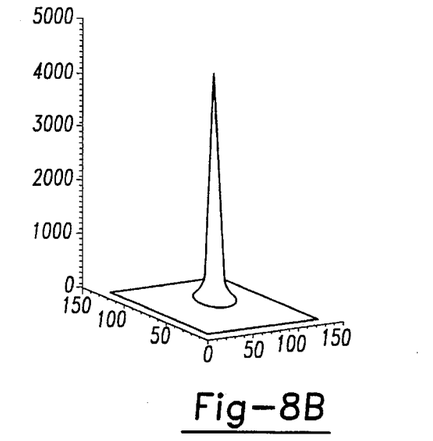
Figure 8C:
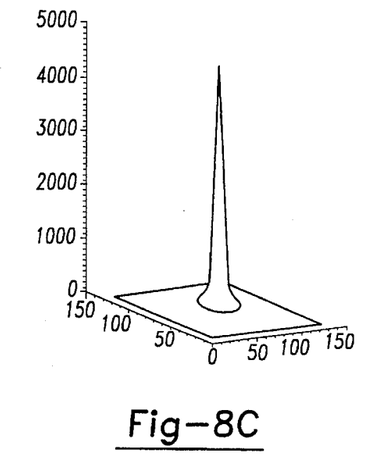
Figure 8E:
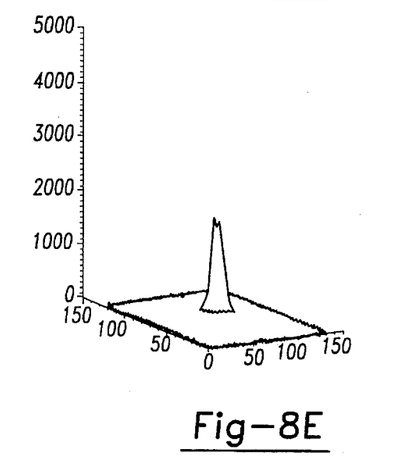
Figure 8F:
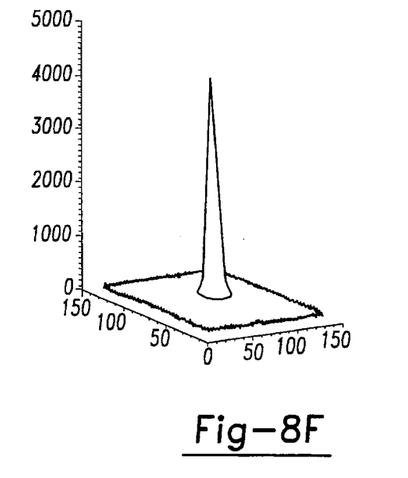

EXAMPLES OF WNN WITH TWO-CHANNEL IMPLEMENTATION:

Two-channel wavelet transform is used as an example of said assembly 10 and for evaluation. It was used in this work for the decomposition of an image into components at multiple scales. The block diagram of two-channel tree-structured wavelet transform (TSWT) for image decomposition is shown in FIG. 2, and for image reconstruction is shown in FIG. 6. The resolution level is 2, the basis functions for $f(x,y) \in V_2$, where $V_2$ is the subspace spanned by $\{\Phi_{m,n}(x)\}_{n=-\infty}^{n=+\infty}$ and $V_2 = V_1 \oplus W_1$, can be ordered by $$\Phi_1(x)\Phi_1(y), \Phi_1(x)\psi_1(y)$$

$$\psi_1(x)\Phi_1(y), \psi_1(x)\psi_1(y) \quad (32)$$

Corresponding to the matrix of the basis functions, (13) can be represented by the following block-matrix $$A_{1x}f(x,Y)A_{1y}f(x,Y), A_{1x}f(x,y)B_{1y}f(x,)$$

$$B_{1x}f(x,Y)A_{1y}f(x,y), B_{1x}f(x,y)B_{1y}f(x,y) \quad (33)$$

where $A_{1x}f(x,y)A_{1y}f(x,y)$ corresponds to low frequencies in horizontal and vertical directions, $A_1xf(x,y)B_{1y}f(x,y)$ corresponds to low frequencies in horizontal direction and high frequencies in vertical directions, $B_{1x}f(x,y)A_{1y}f(x,y)$ corresponds to high frequencies in horizontal direction and low frequencies in vertical directions and $B_{1x}f(x,y)B_{1y}f(x,y)$ corresponds to high frequencies in both directions.

In order to remove noise and preserve the diagnostic features, the following criterion is used;

$$e(f) \frac{1}{L^2} \|F\|_1 = \frac{1}{L^2} \sum_{i=1}^{L} \sum_{J=1}^{L} |f_k(i,j)| \quad (34)$$

where $F = (f_1, f_2, \ldots, f_{M \times M})$, as the energy function to locate dominant frequency/resolution channel. Eq. (33) is called averaged $l_1$-norm. To calculate the energy of each decomposed image, if the energy of a subimage is significantly smaller than others, we calculate multichannel correlation function which is defined as $$R_f^{kl}(i,j) = \frac{1}{L^2} \sum_{m=1}^{L} \sum_{n=1}^{L} f_k(i+m, j+n) f_l(i,j) \quad (35)$$

If the correlation function is also significantly smaller than others, we deal with this subimage as noise and abandon it. The wavelet approach makes this computation simple, i.e., all the corresponding resolution channel coefficients are set to zero. The image deconvolution by neural network is only implemented in dominant subimages (dominant frequency/resolution channels). Although there exist other norms such as $l_2$-norm for the energy function, it is found that the $l_1$ and $l_2$ norms make little difference in the final results. The energy function Eq. (33) is chosen due to its simplicity.

Experimental Validation of WNN Method

A Picker Dyna camera 12 (model SX 3000, Picker International, Cleveland, CN) equipped with 511 keV detector shielding and 3/8 inch NaI crystal was employed. A long bore high energy collimator was used for imaging bremsstrahlung; the details of the collimator and imaging protocols have been previously described for our earlier work using the OSNNH filter [3,4,7]. The collimator resolution was comparable to the resolution for single photon detection using high energy photons ($^{32}$P: 1.32 cm FWHM, 2.61 cm FWTM; $^{90}$Y: 1.30 cm FWHM, 2.88 cm FWTM) [3,4]. A wide energy window was used to compensate for the low geometrical efficiency of the collimator and the poor conversion efficiency for bremsstrahlung detection [3,4,7]; the energy window size range was 57–285 keV that also enclosed the characteristic K shell peak. A typical compiler system, such as IBM™ or Sun, may be utilized to implement the filter 10 with the algorithms as described herein.

The measured point spread functions (PSF's), were acquired using a point source (0.00053 cm$^3$), using $^{32}$P and $^{90}$Y taken at several depths in a water tank 20 cm deep at 2 cm intervals as reported by these investigators [3,4,7].

Phantom measurements were performed in the same water tank, 20 cm deep and with an air gap of 5 cm between the tank base and the collimated detector face [3,7]. Two spherical volume sources were employed using thin walled lucite containers (Data Spectrum, Raleigh, N.C., SPECT phantom accessories) with diameters of 6 cm and 3.5 cm with activities of 5.18 and 0.65 GBq of $^{32}$P and 2.50 and 0.53 GBq of $^{90}$Y respectively, in proportion to their volume. These sources were placed at various depths in the water tank at 2 cm intervals in order to measure the effective attenuation coefficient for the raw images and the restored images for the OSNNF and the proposed WNN filter. Images were acquired using a 128×128 matrix with a pixel size of 0.28 cm, 16 bits deep and a present court of 100K/view. The counts per view were similar to that encountered in clinical protocols for bremsstrahlung imaging for planar or SPECT measurements [3,7]. Regions of interest (ROI) were incrementally selected to enclose the image of each source to generate plots of log of counts versus source depth to calculate the attenuation coefficient to generate 3D plots of ROI size, log of counts and source depth.

Simulated Image Data: Simulation of an isolated source with cylindrical geometry, as opposed to spherical geometry, was used, as illustrated in the 3D plot in FIG. 7. To simulate the influence of cross interference of counts between sources of varying size within the field of view of the gamma camera, a simulated image with multiple cylindrical sources was also used. In this case, cylindrical diameters of 0.89, 1.91 3.7 and 5.64 were simulated, corresponding to earlier experimental work on tomographic imaging of beta emitters [17] with the diameters approximately relating to 0.5x, 1x, 2x and 3x FWHM of the detector system resolution and with a small inscribed radius of 5 cm [17]. The relative strengths of the sources are in proportion to their volume. The single isolated source and multiple source case are referenced as Im1 and Im2 in FIG. 8. Two levels of Poisson noise was added to the simulated image with $\sigma_n^2$=64 and $\sigma_n^2$=8. The variance is defined as $\sigma_n^2(i,j)=E(f(i,j))/\lambda$.

Simulated Image Data: FIG. 7 shows the following: (a) the 3D plot of the simulated cylindrical source, (b) the measured point spread function (PSF) for $^{32}$p [7], (c) the original image blurred by the PSF and with the highest level of noise added (d) decomposition of this image using the M=2 wavelet transform into four subimages essentially separating the signal from noise (e) the restored image using the OSNNH filter (7) and finally (f) the restored image using the proposed WNN filter. Visual inspection of the restored images demonstrate that both filters perform equally well while still maintaining the magnitude of the signal and the total counts in the image [7].

The important conclusion, was the comparable performance of the WNN filter that was a factor for four to six faster computationally than the OSNNH filter. For example, the restoration shown in FIG. 5e takes about 36 minutes using OSNNH filter and 8 minutes using WNN (FIG. 5f).

Preliminary Experimental Data: A representative image of the spherical source containing $^{32}$P and $^{90}$Y (diameter 3.5 cm) at 10 cm depth in the water tank and the restored images using the OSNNH and WNN filter are shown in the 3D plots in FIG. 8, respectively. The restored images using both filters were very similar for both radionuclides. The results for the WNN filter suggest similar image restoration as compared to the OSNNH filter, the peak amplitude is slightly higher for the WNN while maintaining total counts in the image [7]. Similar results were observed at each source depth and for both source sizes for P-32 and Y-90.

Figure 9A:
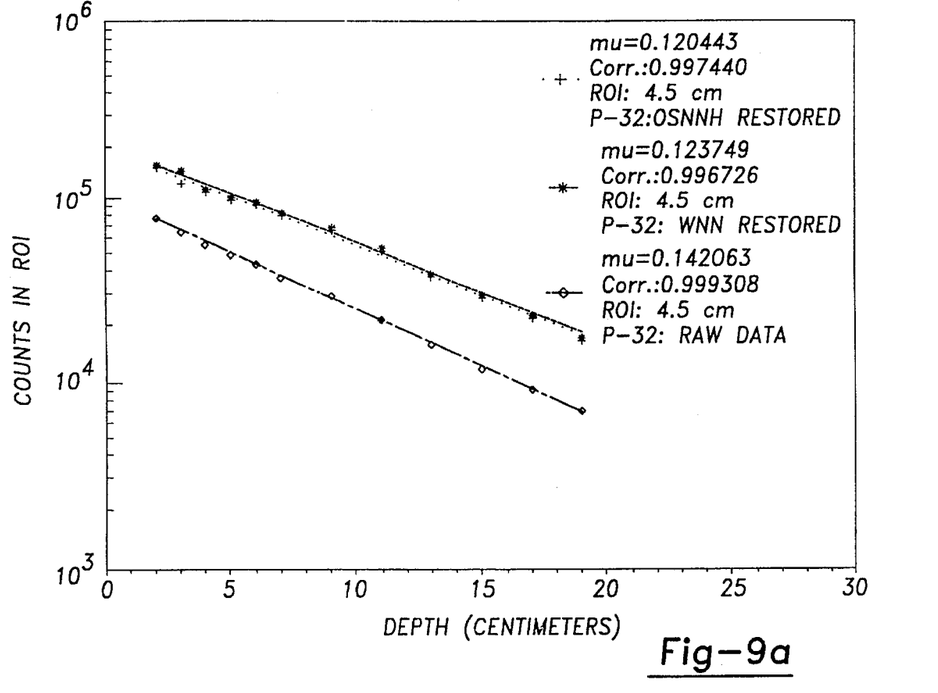
FIGS. 9a–b are attenuation measurements for: (a) $^{32}P$ and (b) $^{90}Y$. Plots of measured counts within regions of interest (ROI's) versus source depth are shown for raw data, OSNNH and WNN filtered images.
Figure 9B:
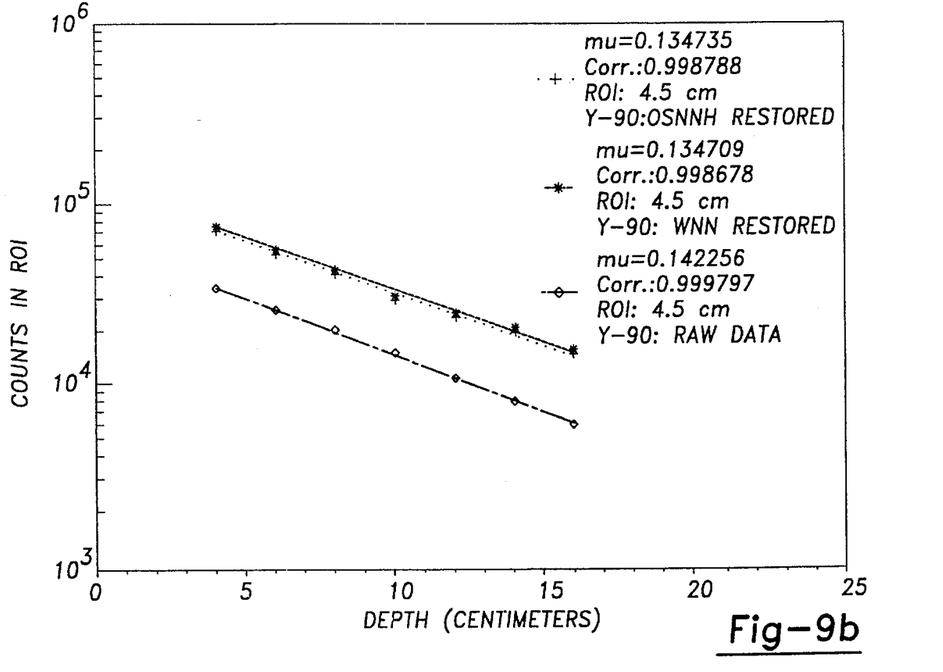
Figure 10:
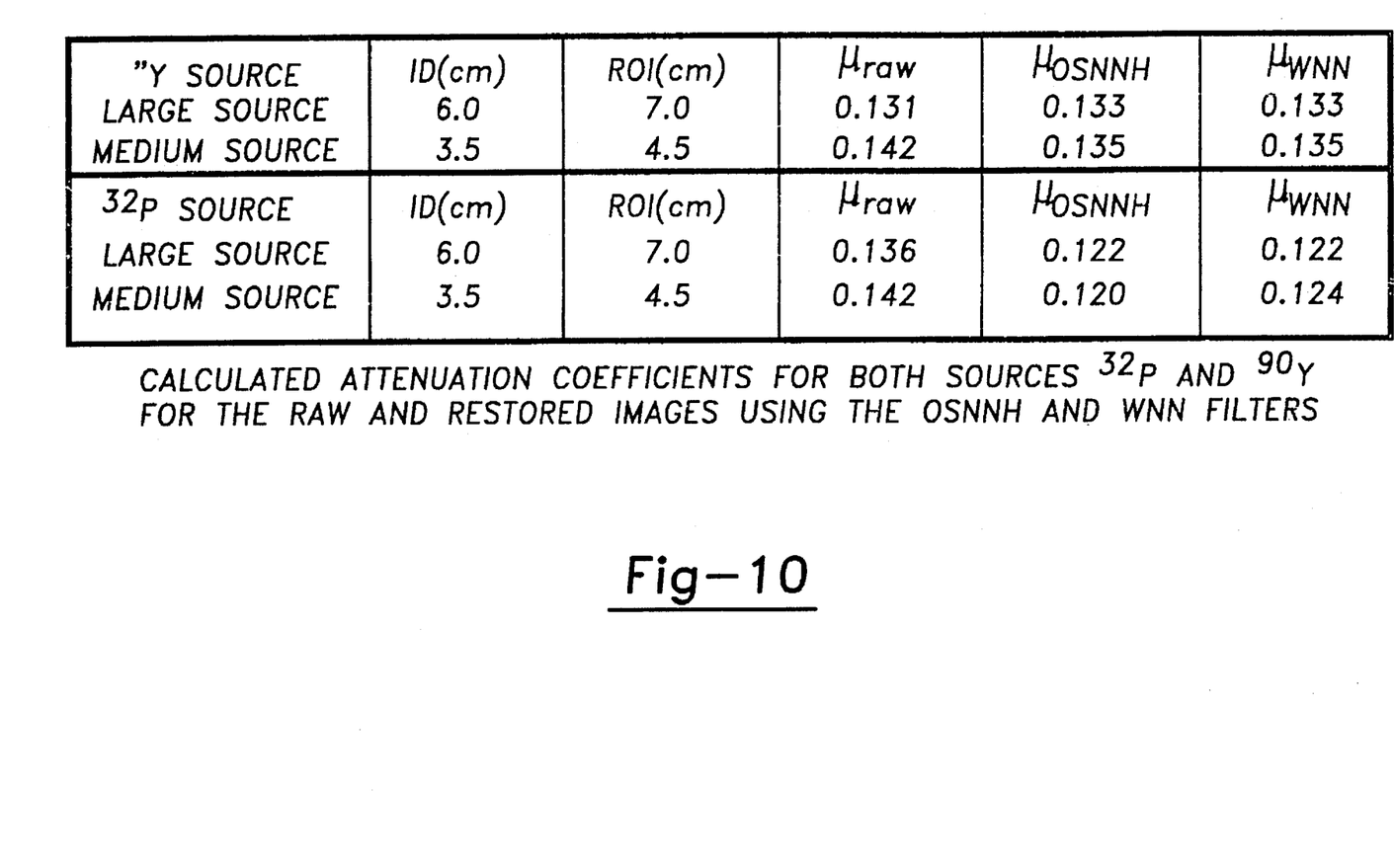
FIG. 10 is a table of calculated attenuation coefficients for use in FIG. 9.

FIG. 9 shows the plot of integrated counts within the ROI with source depth for the 3.5 cm size for the raw data and the restored images using both filters and radionuclides. The size of the ROI was empirically chosen to be 1 cm larger than the cross sectional area of each source. The calculated attenuation coefficients for the restored images for both filters, as shown in FIG. 10, for both source sizes, were essentially within the experimental error of measurement and slightly lower than that obtained for the unprocessed image for each radionuclide.

REFERENCES

[1]. R. J. Jaszczak, R. E. Coleman and F. R. Whitehead; "Physical factors affecting quantitative measurements using camera-based single photon emission computed tomography (SPECT)" IEEE Trans. Nucl. Sci., Vol. NS-28, pp. 69–80, Feb. 1981.

[2]. L. P. Clarke, S. J. Cullom, C. B. Saw, P. K. Penny and M. L. Silbiger "Quantitative ECT: Comparison of Recovery Coefficient and Linearity of Detector Response for Single Phono and Coincidence Detection (F-18, B+511 Kev)" IEEE Transactions on Medical Imaging, March 1986, Vol.5(4), pp177–182.

[3]. L. P. Clarke, S. J. Cullom, R. S. Shaw, C. Reece, B. C. Penney, M. A. King, and M. Silbiger, "Bremsstrahlung Imaging Using the Gamma Camera: Factors Affecting Attenuation," J. Nucl. Med., vol. 33, pp. 161–166, 1992.

[4]. M. A. King, P. W. Doherty, R. B. Schwinger and B. C. Penney "A Wiener filter for nuclear medicine images" Med. Phys. Vol. 10, pp. 876–880, 1983.

[5]. B. C. Penney, M. A. King, R. B. Schwinger, S. P. Baker and P. W. Doherty "Modifying constrained least-squares restoration for application to single photon emission computed tomography projection images" Med. Phys. vol. 15, pp. 334–342, 1988.

[6]. W. Qian, M. Kallergi, L. P. Clarke, "Order-Statistic Neural-Network Hybrid Filters for Gamma Camera Bremsstrahlung Image Restoration," IEEE Transactions on Medical Imaging, March 1993, Vol. 12, No. 1, pp. 58–65.

[7]. R. A. Gonzalo and R. E. Foster, "Detail-preserving ranked-order based filters for image processing," IEEE Trans. Acoust., Speech, Signal Processing, vol. 37(1), pp. 83–98, Jan. 1989.

[8]. Y-T. Zhou, R. Chellappa, A. Vaid, and B. K. Jenkins, "Image Restoration Using a Neural Network," IEEE Trans. ASSP, vol. 36, pp. 1141–1151, 1988.

[9]. H. D. Li, W. Qian, L. P. Clarke, and M. Kallergi. "Neural Network for Maximum Entropy Restoration of Nuclear Medicine Images." Proceedings of the International Conference on Acoustics, Speech, and Signal Processing, Minneapolis, Minn.; Apr. 27–30, 1993.

[10]. J. B. Abbiss, B. J. Brames, and M. A. Fiddy, "Superresolution Algorithms for a Modified Hopfield Neural Network," IEEE Trans. Signal Proc., vol. 39, pp. 1516–1523, 1991.

[11]. W. Qian, L. P. Clarke, M. Kallergi, H. D. Li, R. Velthuizen, R. A. Clark and M. L. Silbiger, "Tree-structured nonlinear filter and wavelet transform for microcalcification segmentation in mammography." Proc. of the SPIE IS&T Conference, San Jose, Calif. Jan. 31–Feb. 4, 1993.

[12]. W. Qian and D. M. Titterington, "Bayesian Image Restoration: An Application to Edge Preserving Surface Recovery", IEEE Trans on Pattern Analysis and Machine Intelligence, Vol. 15, No. 7 PP 748–752, July 1993.

[13]. N. P. Galatsanos and R. T. Chin, "Digital Restoration of Multichannel Images" IEEE Trans. on ASSP Vol. 37, pp. 415–421, March 1989

[14]. G. Wang, J. Zhang and G. W. Pan "Solution of Inverse Problems in Image Processings by Wavelet Expansion" Proceedings of the International Conference on Acoustics, Speech, and Signal Processing, Minneapolis, Minn.; pp. V61–V64, Apr. 27–30, 1993.

[15]. M. R. Banham, H. Gonzalez, Z. P. Galatsanos and A. K Katsaggelos, "Multichannel Restoration of Single Channel Images Using a Wavelet Decomposition" Proceedings of the International Conference on Acoustics, Speech, and Signal Processing, Minneapolis, Minn.; pp. V281–284, Apr. 27–30, 1993.

[16]. Kallergi M., Qian W., Clarke L. P. and Gondeck A. R. "Bremsstrahlung Imaging with the Gamma Camera" Proceedings of SPIE—The International Society for Optical Engineering Conference, Feb. 1992 in Calif., U.S.A.

[17]. I. Daubechies, "Ten lectures on wavelets," CBMS-NSF Regional Conference Series in Applied Mathematics, Vol. 91, SIAM, Philadelphia, 1992.

[18]. S. Mallat, "Multifrequency channel decompositions of images and wavelet models." IEEE Trans. Acoust. Speech, Signal Proc. 37, pp. 2091–2110, 1989.

[19]. S. Mallat, "A theory for multiresolution signal decomposition: the wavelet representation." IEEE Trans. Patt. Anal. Machine Intell. 11(7), pp. 674–693, 1989.

[20]. P. P. Vaidyanathan, 1987. Quadrature mirror filter banks, M-band extensions and perfect-reconstruction technique. IEEE ASSP Mag. 4, pp. 4–20. July, 1987.

[21]. P. P. Vaidyanathan, "Theory and design of M-channel maximally decimated quadrature mirror filters with arbitrary M, having the perfect-reconstruction property", IEEE trans. on ASSP, Vol. 35, No. 4, pp. 476–492, April. 1987.

[22]. W. Qian, L. P. Clarke, H. D. Li, M. Kallergi, R. A. Clark, and M. L. Silbiger, Application of M-Channel Quadrature Mirror Filters for Microcalcification Extraction in Digital Mammography Computerized Medical Imaging and Graphics 18(5): 1994.

What is claimed is:

1. A method of detecting a nuclear image and filtering noise from the detected image, the method including the steps of:

detecting a nuclear image and producing an image signal;

storing the image signal;

decomposing the image signal based on wavelet transform into a plurality of subimages of different resolution to concentrate image noise in at least one of the subimages and to concentrate the image signal in another of the subimages;

selecting dominant subimages based on resolution representative of the nuclear image to eliminate the concentrated noise subimage;

restoring the selected dominant subimages to a restored image of improved resolution by a neural network; and reconstructing the selected dominant subimages to a single high resolution image signal.

2. A method as set forth in claim 1 wherein the decomposing is based on wavelet expansion.

3. A method as set forth in claim 2 wherein the selection of dominant subimages occurs by selecting low frequencies and resolutions of the subimages as the dominant images while eliminating high frequencies and resolutions containing a concentrated amount of noise.

4. A filter assembly for use with a nuclear detector to received nuclear image signals and to increase resolution thereof while decreasing the amount of noise, said assembly comprising:

storing device for detecting and storing a nuclear image signal;

decomposition means for decomposing the nuclear image based on wavelet transform into a plurality of subimages of different resolution to concentrate noise in at least one of the subimages and to concentrate the image signals in another of the subimages;

selection means for selecting dominant subimages based on resolution representative of the nuclear image signal to eliminate the concentrate noise subimage;

restoration means for restoring the selected dominant subimages to a restored image of improved resolution, said restoration means including a neural network; and reconstruction means for reconstructing the selected dominant subimages to a single high resolution image signal.

5. An assembly as set forth in claim 4 further characterized by said decomposition means including decomposing based on wavelet expansion.

6. An assembly as set forth in claim 5 further characterized by said storing means including a nuclear detector and image matrix.

7. An assembly as set forth in claim 6 further characterized by said nuclear detector including a gamma camera.

8. An assembly as set forth in claim 6 further characterized by selecting low frequencies and resolutions of the subimages as the dominant images while eliminating high frequencies and resolutions containing a concentrated amount of noise.

* * * * *